United States Patent [19]

Shimizu et al.

[11] Patent Number: 5,245,059

[45] Date of Patent: Sep. 14, 1993

[54] METHOD FOR THE PREPARATION OF 2,3,5-TRIMETHYLBENZOQUINONE

[75] Inventors: Masao Shimizu; Katsuomi Takehira; Takashi Hayakawa; Hideo Orita, all of Tsukuba, Japan

[73] Assignee: Japan as represented by Director General of Agency of Industrial Science and Technology, Toyoto, Japan

[21] Appl. No.: 318,716

[22] Filed: Mar. 3, 1989

[30] Foreign Application Priority Data

Mar. 16, 1988 [JP] Japan .................................. 63-62878
Mar. 25, 1988 [JP] Japan .................................. 63-72727

[51] Int. Cl.$^5$ ............................................. C07C 50/04
[52] U.S. Cl. ...................................................... 552/310
[58] Field of Search ...................... 260/396 R; 552/310

[56] References Cited

U.S. PATENT DOCUMENTS 4,482,493 11/1984 Matsumoto et al. ............... 552/310
5,041,572 8/1991 Hoercher et al. ................... 552/310
5,104,996 4/1992 Hirose et al. ......................... 552/310

FOREIGN PATENT DOCUMENTS 55-30781 8/1980 Japan .

OTHER PUBLICATIONS

Korenskii et al., Zh. Obshch. Khim., vol. 55 (1985) pp. 1750–1754.

Primary Examiner—José G. Dees
Assistant Examiner—Dwayne C. Jones
Attorney, Agent, or Firm—Wenderoth, Lind & Ponack

[57] ABSTRACT

2,3,5-Trimethyl-p-benzoquinone is prepared advantageously by the catalytic oxidation of 2,3,5- or 2,3,6-trimethylphenol with hydrogen peroxide in an organic solvent, which is preferably acetic acid, in the presence of a catalyst which is a heteropolyacid of silicon or phosphorus as the center atom selected from phosphomolybdic acid, silicomolybdic acid, phosphotungstic acid and silicotungstic acid. The reaction proceeds rapidly even at room temperature to give the product in a high yield so that the method is industrially advantageous in addition to the advantages in respect of the inexpensiveness of the reactants and catalyst and absence of any noxious byproducts which may cause environmental pollution.

11 Claims, No Drawings

METHOD FOR THE PREPARATION OF 2,3,5-TRIMETHYLBENZOQUINONE

BACKGROUND OF THE INVENTION

The present invention relates to a method for the preparation of 2,3,5-trimethylbenzoquinone or, more particularly, to an efficient method for the preparation of 2,3,5-trimethylbenzoquinone by the oxidation of 2,3,5- or 2,3,6-trimethylphenol in the presence of a specific catalyst.

As is known, 2,3,5-trimethylbenzoquinone is an important organic compound useful as a starting material in the synthetic preparation of vitamin E and other valuable chemicals. One of the conventional methods industrially undertaken for the preparation of 2,3,5-trimethylbenzoquinone includes the steps of sulfonation of 2,3,6-trimethylphenol as the starting material and oxidation of the sulfonation product by using manganese dioxide (see, for example, West German Patents No. 1,932,362 and No. 2,225,543) as an oxidizing agent. Although 2,3,6-trimethylphenol is an inexpensive material manufactured by the orthomethylation of m-cresol or by the oxidation of pseudocumene and available in any large quantities, the above mentioned manufacturing process of 2,3,5-trimethylbenzoquinone has problems in respect of the by-product to be disposed of as a waste material and the relatively high production cost.

Alternatively, it is also known that 2,3,5-trimethylbenzoquinone can be prepared by the direct oxidation of 2,3,5- or 2,3,6-trimethylphenol and many attempts and proposals have been made hitherto in connection with selection of the oxidizing agent and the catalyst for the oxidation reaction. Examples of the oxidizing agent proposed so far include nitric acid taught in Japanese Patent Publication 56-95145, perbenzoic acid taught in Japanese Patent Publication 59-39847, hypohalogenous acids taught in Japanese Patent Publication 60-81135 and the like. These methods also are not quite satisfactory as an industrial method in respect of evolution of toxic gases, expensiveness of the oxidizing agent and formation of by-products. It is also known that hydrogen peroxide can be used as the oxidizing agent and this method is the most promising as an industrial method because hydrogen peroxide is relatively inexpensive and the by-product formed from the oxidizing agent is water alone absolutely without problems of environmental pollution.

The oxidation reaction of 2,3,5- or 2,3,6-trimethylphenol with hydrogen peroxide to give 2,3,5-trimethylbenzoquinone is promoted by a catalyst and a method is known to use a salt of metal such as ruthenium and the like (see, for example, Chem. Lett., volume 24 (1983), page 5246 and European Patent Application 107176). This method is, however, disadvantageous due to the expensiveness of the rare metal as the constituent of the catalyst and relatively low yield of the desired product.

SUMMARY OF THE INVENTION

The present invention accordingly has an object to provide a novel and efficient method for the preparation of 2,3,5-trimethylbenzoquinone by the oxidation of 2,3,5- or 2,3,6-trimethylphenol with hydrogen peroxide as the oxidizing agent in the presence of a catalyst.

Thus, the method of the present invention for the preparation of 2,3,5-trimethylbenzoquinone comprises: oxidizing 2,3,5-trimethylphenol or 2,3,6-trimethylphenol with hydrogen peroxide in the presence of a catalyst which is a heteropolyacid of phosphorus or silicon containing molybdenum or tungsten.

DETAILED DESCRIPTION OF THE PREFERRED EMBODIMENTS

As is described above, the most characteristic feature of the inventive method consists in the use of a heteropolyacid as the catalyst and the desired product of 2,3,5-trimethylbenzoquinone is obtained easily by merely agitating a reaction mixture containing the starting material, oxidizing agent and catalyst in an organic solvent under mild conditions so that the method is industrially advantageous because the process is simple and without any danger.

Hydrogen peroxide used as the oxidizing agent in the inventive method is used in the form of an aqueous solution. The concentration of the aqueous solution of hydrogen peroxide is not particularly limitative and commercially available solutions containing 30% by weight of hydrogen peroxide are suitable. Aqueous solutions containing hydrogen peroxide in a higher concentration of 50 to 60% can also be used. The amount of the hydrogen peroxide used in the inventive method is usually in the range from 1 to 30 times or, preferably, from 2 to 10 times the stoichiometric amount required for the reaction.

The heteropolyacid used as the catalyst in the inventive method is exemplified by silicomolybdic acid, silicotungstic acid, phosphomolybdic acid and phosphotungstic acid. Salts of these acids such as ammonium salts and alkali metal salts are also suitable. The amount of the catalyst added to the reaction mixture is 0.05 mole or smaller or, preferably, in the range from 0.01 to 0.03 mole per mole of the 2,3,5- or 2,3,6-trimethylphenol as the starting material though not particularly limitative.

The organic solvent used as the reaction medium in the inventive method should be miscible with the aqueous solution of hydrogen peroxide as the oxidizing agent in order that the reaction proceeds in a homogeneous phase. Examples of the organic solvent suitable for use having miscibility with water include carboxylic acids such as formic, acetic and propionic acids, acetonitrile, methyl alcohol, ethyl alcohol, acetone, N,N-dimethylformamide and the like, of which carboxylic acids such as acetic acid are preferable. The amount of the solvent is such that the concentration of the 2,3,5- or 2,3,6-trimethylphenol as the starting material in the reaction mixture is in the range from 0.05 to 1.0 mole/liter or, preferably, from 0.1 to 0.5 mole/liter. The concentration of the hydrogen peroxide as the oxidizing agent in the reaction mixture is preferably in the range from 3 to 8% by weight as $H_2O_2$. The concentration of water, which is unavoidably introduced into the reaction mixture in the form of an aqueous solution of hydrogen peroxide, should not exceed 30% by weight based on the amount of the solvent although water in a small amount has no particular adverse influence on the proceeding of the reaction.

The temperature of the reaction mixture is in the range from 0° to 70° C. or, preferably, from 10° to 35° C. and the reaction can proceed with a sufficiently high velocity even at room temperature requiring no exact control of the temperature. The reaction is usually complete within 1 to 15 hours though dependent on the concentration of the aqueous hydrogen peroxide solution and the amount of used catalyst.

As the reaction proceeds in the reaction mixture, the color thereof turns yellow. The reaction mixture, after completion of the reaction, is diluted with water and the reaction product is extracted therefrom with an organic solvent immiscible with water such as methylene chloride. The extract is dried over a drying agent such as anhydrous magnesium sulfate and then freed from the solvent by distillation to leave the desired 2,3,5-trimethylbenzoquinone as the product which can be identified by gas chromatography and NMR analysis to give a retention time and NMR spectrum identical, respectively, with those of a standard reagent of 2,3,5-trimethylbenzoquinone.

As is understood from the above given description, the method of the invention is advantageous as an industrial manufacturing process of 2,3,5-trimethylbenzoquinone since the product is obtained from 2,3,5- or 2,3,6-trimethylphenol in a single step reaction in a high yield without the disadvantages in the prior art methods in respect of the waste material produced as a by-product, expensiveness of the catalyst and low yield of the product.

In the following, the method of the present invention is described in more detail by way of examples. The heteropolyacids used in the following experiments as the catalyst include phosphomolybdic acid, silicomolybdic acid, phosphotungstic acid and silicotungstic acid, which are referred to as the catalysts I, II, III and IV, respectively, hereinbelow.

EXAMPLES 1 to 4.

Into a glass flask were introduced 272 mg (2 m moles) of 2,3,5-trimethylphenol and 100 mg of one of the catalysts mentioned above dissolved in 10 ml of acetic acid and 2 ml of a 60% aqueous solution of hydrogen peroxide were added dropwise to the reaction mixture in the flask. The reaction mixture was agitated for 5 hours in an atmosphere of nitrogen gas at 30° C. After completion of the reaction, the reaction mixture was diluted with addition of 50 ml of water and extracted three times each with 20 ml of methylene chloride. The extracts as combined were dried over anhydrous magnesium sulfate and analyzed by gas chromatography for the content of 2,3,5-trimethylbenzoquinone as the product. The results are shown in the table below which includes the % reaction, i.e. % of the reacted starting material, yield in %, i.e. the amount of the product relative to the reacted starting material, and selectivity in %, i.e. % of the reacted starting material converted into the desired product.

EXAMPLES 5 to 8.

The experimental procedure was substantially the same as in the preceding examples except that the reaction time was 3 hours instead of 5 hours. The results are summarized in the table.

EXAMPLES 9 to 12.

The experimental procedure was substantially the same as in Examples 1 to 4 except that the concentration of the aqueous hydrogen peroxide solution was 30% instead of 60%. The results are summarized in the table.

COMPARATIVE EXAMPLES 1 to 3.

The experimental procedures in Comparative Examples 1, 2 and 3 were substantially the same as in Example 1, Example 9 and Example 9, respectively, excepting omission of the phosphomolybdic acid, replacement of the phosphomolybdic acid with 100 mg (0.56 m mole) of orthomolybdic acid monohydrate and replacement of the phosphomolybdic acid with 100 mg (0.40 m mole) of orthotungstic acid, respectively. The results are summarized in the table.

EXAMPLES 13 to 16.

The experimental procedure was substantially the same as in Examples 1 to 4 excepting replacement of the 2,3,5-trimethylphenol with the same amount of 2,3,6-trimethylphenol. The results are summarized in the table.

EXAMPLES 17 to 20.

The experimental procedure was substantially the same as in Examples 13 to 16 except that the concentration of the aqueous hydrogen peroxide solution was 30% instead of 60% and the reaction time was 12 hours instead of 5 hours. The results are summarized in the table.

EXAMPLES 21 to 24.

The experimental procedure was substantially the same as in Examples 17 to 20 except that the reaction time was 5 hours instead of 12 hours. The results are summarized in the table.

COMPARATIVE EXAMPLES 4 to 6.

The experimental procedures in Comparative Examples 4, 5 and 6 were each substantially the same as in Example 3, Example 21 and Example 21, respectively, excepting omission of the phosphomolybdic acid, replacement of the phosphomolybdic acid with 7.2 mg (0.04 m mole) of orthomolybdic acid monohydrate and replacement of the phosphomolybdic acid with 10 mg (0.04 m mole) of orthotungstic acid. The results are summarized in the table.

EXAMPLES 25 to 32.

The experimental procedure was substantially the same as in Examples 13 to 16 excepting replacement of the acetic acid with the same amount of formic acid in Examples 25 to 28 and of propionic acid in Examples 29 to 32. The results are summarized in the table.

TABLE

|  |  | Catalyst | % reaction | Yield, % | Selectivity, % |
|---|---|---|---|---|---|
| Example | 1 | I | 100.0 | 72.0 | 72.0 |
|  | 2 | II | 100.0 | 70.9 | 70.9 |
|  | 3 | III | 100.0 | 57.8 | 57.8 |
|  | 4 | IV | 100.0 | 58.7 | 58.7 |
|  | 5 | I | 100.0 | 68.8 | 68.8 |
|  | 6 | II | 93.1 | 70.6 | 76.0 |
|  | 7 | III | 99.9 | 59.9 | 59.9 |
|  | 8 | IV | 99.9 | 59.6 | 59.6 |
|  | 9 | I | 77.0 | 49.9 | 64.8 |
|  | 10 | II | 95.7 | 64.5 | 67.5 |
|  | 11 | III | 72.2 | 41.6 | 57.7 |
|  | 12 | IV | 95.7 | 64.5 | 67.5 |
|  | 13 | I | 99.9 | 78.3 | 78.3 |
|  | 14 | II | 96.2 | 66.6 | 69.2 |
|  | 15 | III | 93.7 | 63.2 | 67.5 |
|  | 16 | IV | 99.9 | 64.0 | 64.0 |
|  | 17 | I | 99.9 | 60.9 | 60.9 |
|  | 18 | II | 99.9 | 66.7 | 66.7 |
|  | 19 | III | 94.6 | 56.6 | 59.8 |
|  | 20 | IV | 96.6 | 66.0 | 68.4 |
|  | 21 | I | 79.4 | 61.5 | 77.5 |
|  | 22 | II | 59.2 | 59.2 | 100.0 |
|  | 23 | III | 60.8 | 43.5 | 71.5 |
|  | 24 | IV | 44.6 | 44.6 | 100.0 |
|  | 25 | I | 99.9 | 72.0 | 72.0 |
|  | 26 | II | 99.9 | 63.1 | 63.1 |

TABLE-continued

| | | Catalyst | % reaction | Yield, % | Selectivity, % |
|---|---|---|---|---|---|
| | 27 | III | 100.0 | 54.7 | 54.7 |
| | 28 | IV | 100.0 | 45.2 | 45.2 |
| | 29 | I | 99.9 | 62.3 | 62.3 |
| | 30 | II | 99.9 | 63.5 | 63.5 |
| | 31 | III | 94.4 | 49.8 | 52.8 |
| | 32 | IV | 99.9 | 36.8 | 36.8 |
| Comparative Example | 1 | None | 61.9 | 47.1 | 76.1 |
| | 2 | See text | 99.9 | 33.6 | 33.6 |
| | 3 | See text | 91.7 | 15.1 | 16.5 |
| | 4 | None | 30.3 | 24.5 | 80.9 |
| | 5 | See text | 23.4 | 18.7 | 80.1 |
| | 6 | See text | 65.1 | 21.1 | 32.4 |

What is claimed is:

1. A method for the preparation of 2,3,5-trimethylbenzoquinone which comprises:

oxidizing 2,3,5-trimethylphenol or 2,3,6-trimethylphenol with hydrogen peroxide in a reaction mixture containing a heteropolyacid of phosphorus or silicon as the center atom containing molybdenum or tungsten or an ammonium or alkali metal salt thereof as a catalyst.

2. The method for the preparation of 2,3,5-trimethylbenzoquinone as claimed in claim 1 wherein the heteropolyacid is selected from the group consisting of phosphomolybdic acid, silicomolybdic acid, phosphotungstic acid and silicotungstic acid.

3. The method for the preparation of 2,3,5-trimethylbenzoquinone as claimed in claim 1 wherein the reaction mixture is a solution of 2,3,5-trimethylphenol or 2,3,6-trimethylphenol, hydrogen peroxide in the form of an aqueous solution and the catalyst in an organic solvent.

4. The method for the preparation of 2,3,5-trimethylbenzoquinone as claimed in claim 3 wherein the organic solvent has miscibility with water.

5. The method for the preparation of 2,3,5-trimethylbenzoquinone as claimed in claim 4 wherein the organic solvent having miscibility with water is selected from the group consisting of formic acid, acetic acid, propionic acid, acetonitrile, methyl alcohol, ethyl alcohol, acetone and N,N-dimethylformamide.

6. The method for the preparation of 2,3,5-trimethylbenzoquinone as claimed in claim 5 wherein the organic solvent having miscibility with water is selected from the group consisting of formic acid, acetic acid and propionic acid.

7. The method for the preparation of 2,3,5-trimethylbenzoquinone as claimed in claim 6 wherein the organic solvent is acetic acid.

8. The method for the preparation of 2,3,5-trimethylbenzoquinone as claimed in claim 1 wherein the amount of the hydrogen peroxide is in the range from 1 to 30 times of the stoichiometric amount.

9. The method for the preparation of 2,3,5-trimethylbenzoquinone as claimed in claim 1 wherein the amount of the catalyst is in the range from 0.01 to 0.03 mole per mole of the 2,3,5-trimethylphenol or 2,3,6-trimethylphenol.

10. The method for the preparation of 2,3,5-trimethylbenzoquinone as claimed in claim 1 wherein the reaction mixture is kept at a temperature in the range from 10° to 35° C.

11. The method for the preparation of 2,3,5-trimethylbenzoquinone as claimed in claim 1 wherein the reaction mixture contains 2,3,5-trimethylphenol or 2,3,6-trimethylphenol in a concentration in the range from 0.05 to 1.0 mole/liter.

* * * * *